United States Patent [19]
Allington et al.

[11] Patent Number: 5,094,753
[45] Date of Patent: Mar. 10, 1992

[54] APPARATUS AND METHOD FOR SUPERCRITICAL FLUID EXTRACTION

[75] Inventors: Robert W. Allington; Dale L. Clay; Daniel G. Jameson; Robin R. Winter, all of Lincoln, Nebr.

[73] Assignee: Isco, Inc., Lincoln, Nebr.

[21] Appl. No.: 553,119

[22] Filed: Jul. 13, 1990

[51] Int. Cl.$^5$ .............................................. B01D 11/00
[52] U.S. Cl. ...................................... 210/634; 422/256
[58] Field of Search ................ 210/634; 203/16, 19; 422/256-260

[56] References Cited

U.S. PATENT DOCUMENTS 4,770,780  9/1988  Moses ................................. 210/634

Primary Examiner—Frank Sever
Attorney, Agent, or Firm—Vincent L. Carney

[57] ABSTRACT

An apparatus for supercritical fluid extraction incorporates a removable extraction cartridge which in operation has insignificant pressure difference between its inside and outside walls. Because of the low pressure difference, the extraction cartridge need not have the strength to withstand significant pressure and can be made out of molded plastic for disposable use as well as stainless steel and machined plastic for reusability. The extraction cartridge can be removed and opened for sample access without the use of tools. The outside of the cartridge can be purged after it is installed in a heated high pressure vessel to remove contamination from its exterior.

8 Claims, 12 Drawing Sheets

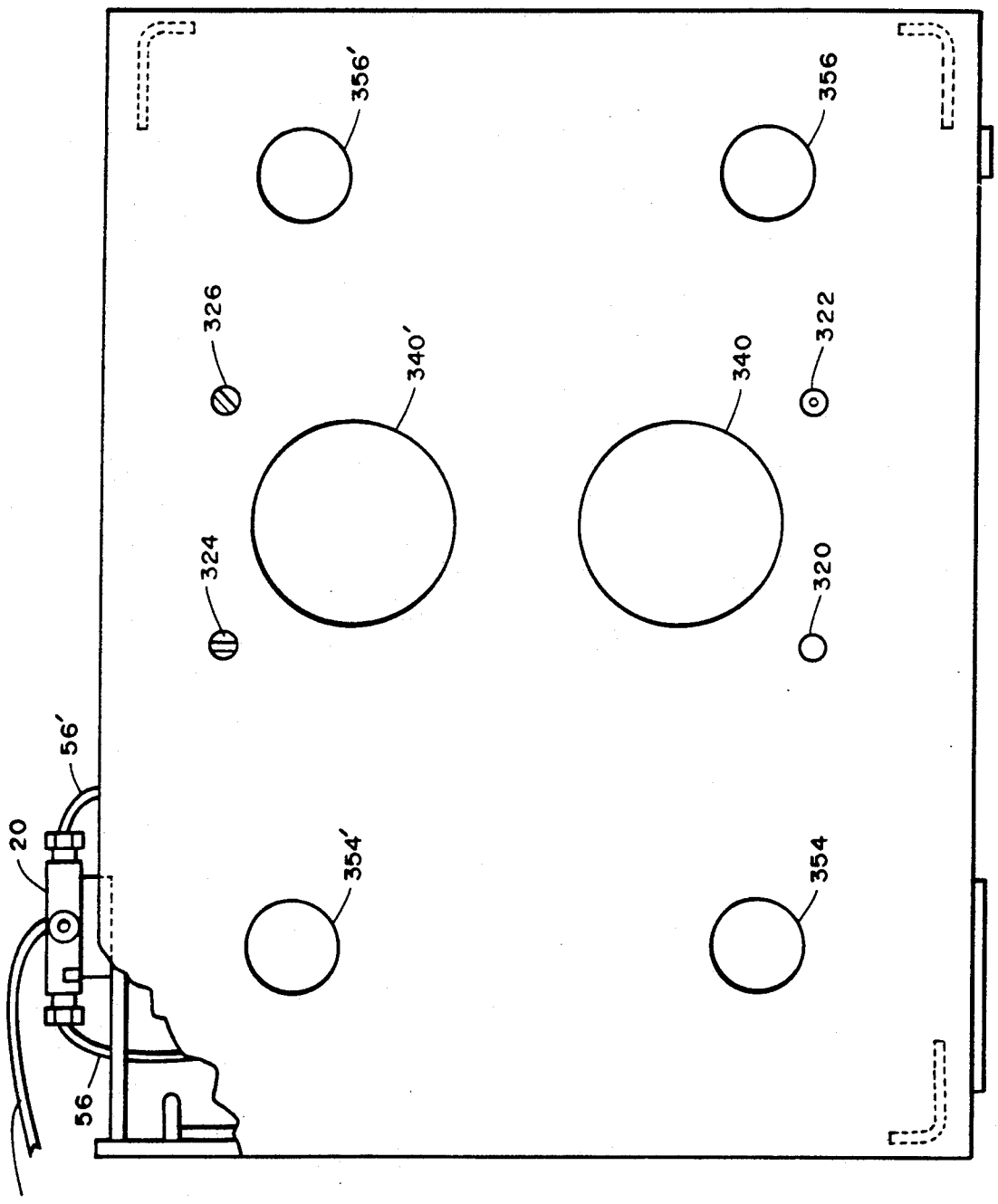

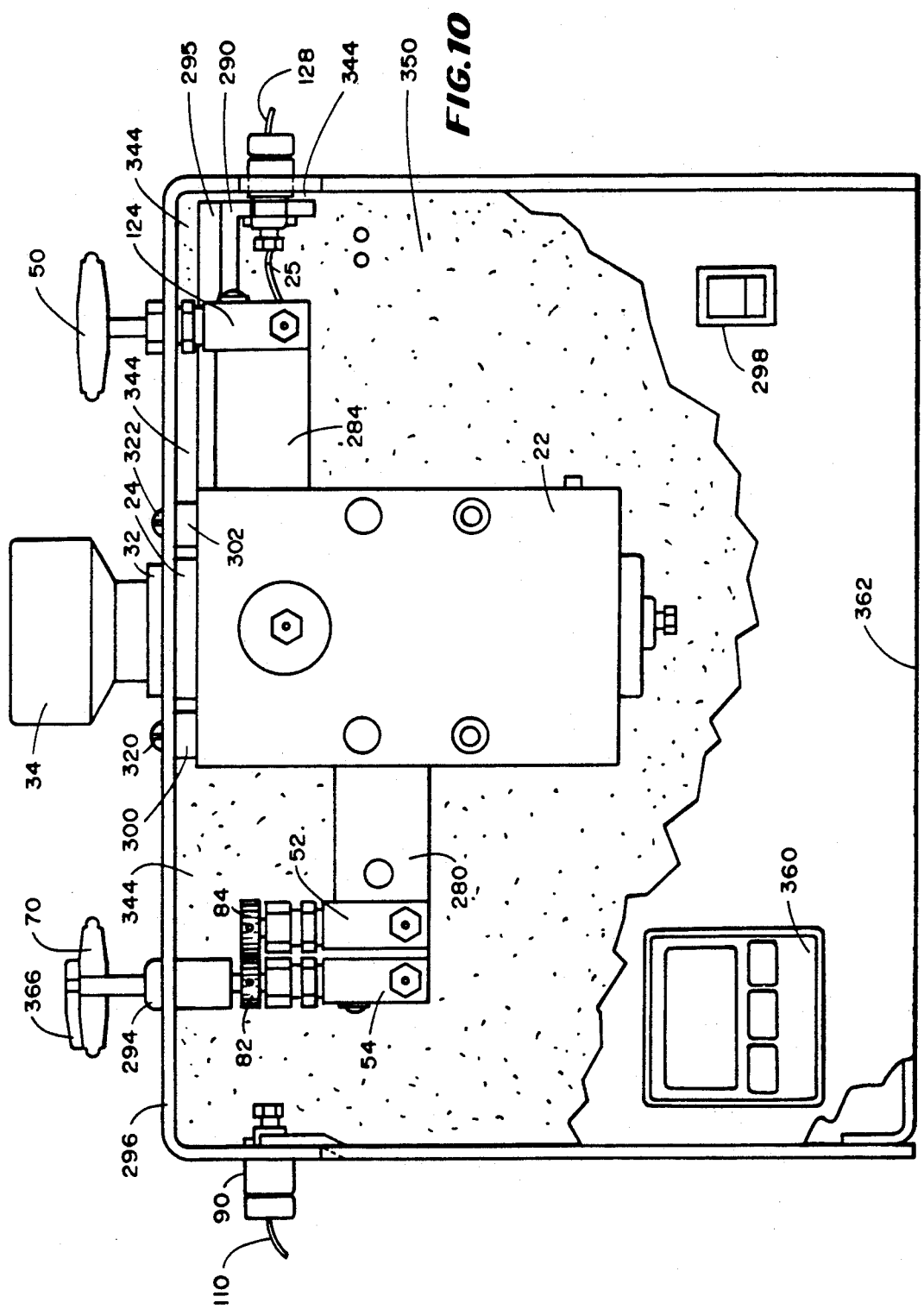

APPARATUS AND METHOD FOR SUPERCRITICAL FLUID EXTRACTION

BACKGROUND OF THE INVENTION

This invention relates to supercritical fluid extraction.

In supercritical fluid extraction, an extraction vessel is held at a temperature above the critical point and is supplied with fluid at a pressure above the critical pressure. Under these conditions the fluid within the extraction vessel is a supercritical fluid. In one type of apparatus for supercritical extraction, there is a specially constructed extraction vessel within a source of heat.

A prior art apparatus for supercritical extraction of this type is described by B. W. Wright, et. al., in *ANAL. CHEM.* 59, 38-44 (January 1987) using a glass-lined extraction chamber within a bolted stainless steel extraction vessel heated in an oven. This type of extraction apparatus has the disadvantages of: (1) requiring time consuming steps to open the pressurized extraction vessel before use to insert the sample and again to open it after use to remove the spent sample; and (2) under some circumstances, requiring the handling of a hot extraction vessel.

SUMMARY OF THE INVENTION

Accordingly, it is an object of the invention to provide a novel supercritical extraction technique;

It is a still further object of the invention to provide a novel supercritical extraction apparatus;

It is a further object of the invention to provide a supercritical extraction technique which is able to use less expensive containers for samples to be extracted than prior techniques;

It is a further object of the invention to provide a supercritical extraction technique which is faster and more convenient than prior techniques;

It is a still further object of the invention to provide a supercritical extraction apparatus in which the sample to be extracted may be more easily and more quickly inserted into the extraction apparatus and removed therefrom after extraction than heretofor possible.

In accordance with the above and further objects of the invention, a supercritical fluid extraction system includes a cartridge capable of holding the sample to be extracted and a pressure vessel into which the cartridge fits. The pressure vessel fits into a heater and the cartridge removably clips to a breech plug that seals the pressure vessel. There are separate outlets for the cartridge and pressure vessel to permit equalization of pressure on the inside and outside of the cartridge without contamination from impurities outside the cartridge but inside the pressure vessel.

The cartridge: (1) may be removed by a handle that is separated from the cartridge by a thermal barrier and extends outside of the pressure vessel so that the cartridge may be removed by the handle even though the cartridge is still hot; (2) receives the supercritical fluid at a pressure similar to the pressure in the pressure vessel and at substantially the same time so that the cartridge may be made of plastic and need not be excessively strong since its internal pressure is matched by the pressure outside of it; and (3) is easily fastened to a plug for the pressure vessel and the combination is easily inserted into the pressure vessel and removed from it.

A heating block for heating the cartridge is mounted to hang from the cabinet for the apparatus and the valves and tubing used in supercritical fluid extraction are mounted close enough to be heated by it to avoid premature condensation. The heater is press fit into the pressure vessel and the cartridge fits into the pressure vessel with only slight clearance to reduce heat loss and increase speed of operation.

In operation, the sample to be extracted is placed within the cartridge and the cartridge inserted into a pressure vessel. Upon insertion, one of two outlet fittings communicates with the interior of the cartridge and the other with the interior of the pressure vessel outside the cartridge. A handle is attachable which resists heat and extends outside the pressure vessel beyond the seal of the pressure vessel. An inlet to the pressure vessel communicates with the outlet of a pump which pumps the supercritical fluid through a path that heats it and into the interior of the pressure vessel and extraction cartridge.

To remove any contaminants from outside of the cartridge, the outlet that communicates within the inside of the pressure vessel and outside of the cartridge, permits the supercritical fluid to cleanse the outside of the cartridge and the inside walls of the pressure vessel from contaminants as it flows outwardly to a contaminant collector. For extraction, the supercritical fluid flows into the cartridge and out of a fitting that communicates with the interior of the cartridge. The extracted material, sometimes referred to as extractant or analyte, flows in solution to a collector for the extractant.

As can be understood from the above description, the supercritical extraction technique has several advantages, such as for example: (1) it is more convenient than prior art extractors; (2) it includes a self-cleaning feature; and (3) it includes as one of its components a disposable inexpensive cartridge to hold the samples.

One reason it is convenient to use is because the cartridge containing the spent sample can be removed while the cartridge is hot because there is a handle that resists being heated and extends outside of the pressure vessel for removal of the cartridge. Another reason it is convenient to use is that it is easier to open the cartridge and pressure vessel since there are no bolts or the like, and in some embodiments, the cartridge is disposable. This convenience is significant because it reduces the time of extraction materially.

It is less expensive because there is pressure equalization within the extractor and the pressure vessel even though it permits purging of the pressure vessel and extraction through separate outlets. A reduction in cost is obtained because plastic cartridges or weaker metal cartridges may be used since the cartridge does not have to withstand a high pressure difference.

DESCRIPTION OF THE DRAWINGS

The above noted and other features of the invention will be better understood from the following detailed description when considered with reference to the accompanying drawings in which:

FIG. 10 is an elevational, front, broken-away view of the dual extractor of FIGS. 5-9 mounted into a metal cabinet with insulation to facilitate in keeping its critical components at a proper elevated temperature;

FIG. 11 is a plan view, partly broken away of the embodiment of FIG. 10;

DETAILED DESCRIPTION

Figure 1:
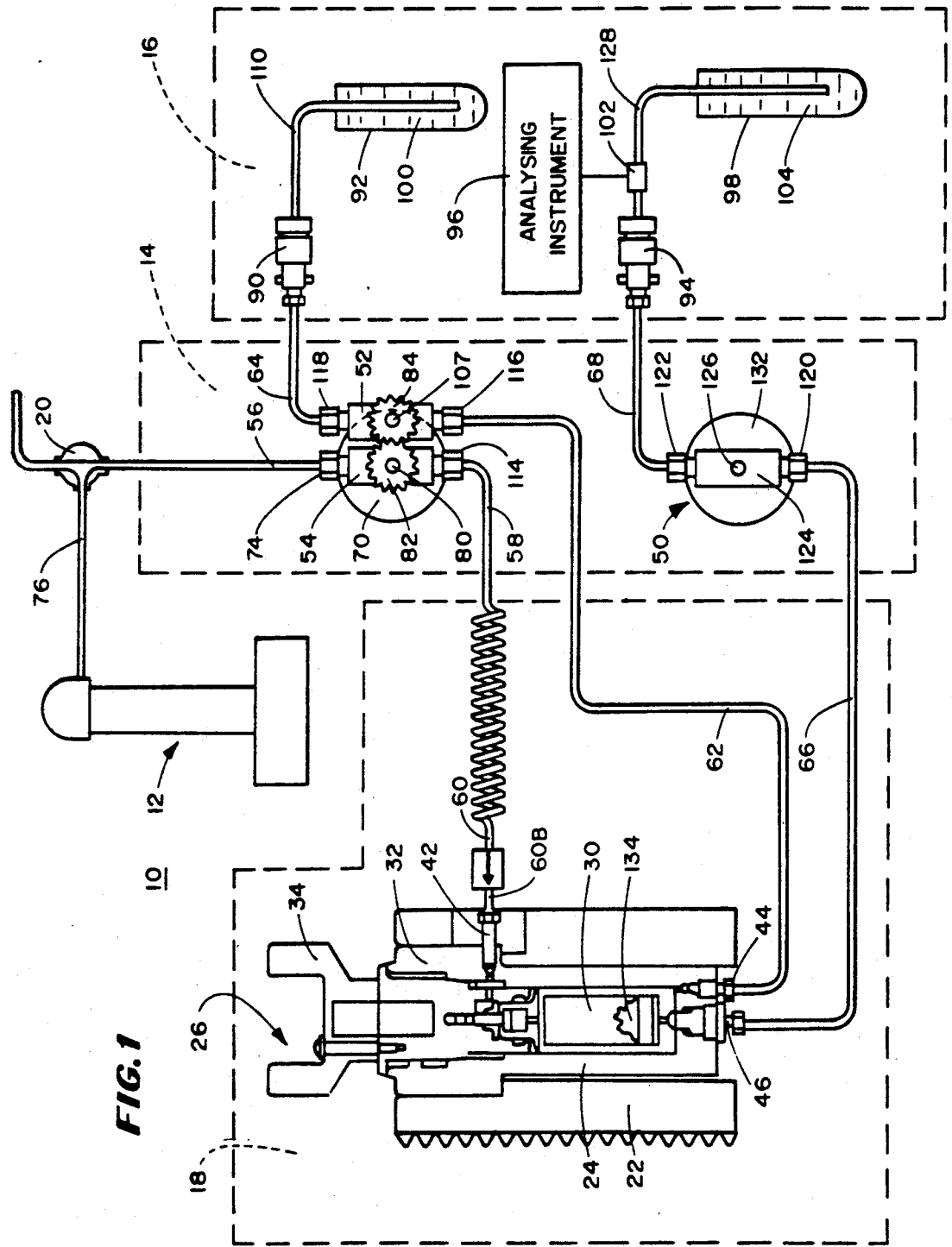
FIG. 1 is a schematic diagram illustrating the operation of a single supercritical fluid extraction system according to the invention.

In FIG. 1, there is shown a schematic fluidic diagram of one channel of a dual-channel supercritical fluid extraction system 10 having a pumping system 12, a valve system 14, a collector system 16 and a pressure vessel and fluid-extraction assembly 18. The pumping system 12 communicates with two extraction cartridges within the pressure vessel and fluid-extraction assembly 18 and for this purpose is connected through a tee joint 20 to two identical valve systems, one of which is shown at 14. Each valve system communicates with a different one of two inlets for the corresponding one of two extraction cartridges.

The pumping system 12 itself is not part of the invention except insofar as it cooperates with the collector system 16, valve systems 14 and pressure-vessel and fluid-extraction assembly 18. Any pumping system capable of providing the flow rates and pressures described herein is suitable and one such system is sold by Isco, Inc., P.O. Box 5347, Lincoln, Nebr. 68505, under the designation Isco Model 260D Pump.

The valve system 14 and a second valve system (not shown in FIG. 1) which is connected to the other branch of the tee joint 20 are each connected to two different collector systems 16, one of which is shown in FIG. 1, and to different ones of the two extraction cartridges in the pressure-vessel and fluid-extraction assembly 18 so that, two extraction operations can be performed at the same time using the same pumping system 12. With this arrangement, the valve system 14 causes: (1) supercritical fluid to flow from the pumping system 12 into a space between a cartridge and the interior of the pressure vessel of the pressure-vessel and fluid-extraction assembly 18 for purging the outside of the cartridge and the inside of the pressure vessel; and (2) applies supercritical fluid through the cartridge for extraction of a sample 134 therein. Because the fluid is applied both to the interior of the cartridge and the exterior, the cartridge does not have to withstand a high pressure difference between its interior and exterior and can be made economically.

In addition to controlling the flow of fluid into the pressure-vessel and fluid-extraction assembly 18, the valve system 14 controls the flow of: (1) purging supercritical fluid from the space between the cartridge and interior of the vessel to the collection system 16 or to a vent; and (2) the extractant from the interior of the cartridge to the collection system 16 for separate collection.

To hold sample 134 during extraction process, the pressure-vessel and fluid-extraction assembly 18 includes a heating block 22, a pressure vessel 24 and a cartridge and plug assembly 26 with the cartridge and plug assembly 26 extending into the pressure vessel 24. The pressure vessel 24 fits within the heating block 22 for easy assembly and disassembly. With this arrangement, the heater block 22 maintains the fluids within the pressure-vessel and fluid-extraction assembly 18 at supercritical fluid temperature and pressure for proper extraction.

The cartridge and plug assembly 26 includes an extraction cartridge assembly 30, a breech plug 32 and a knob 34 which are connected together so that: (1) the pressure vessel 24 is easily sealed with the breech plug 32; (2) the extraction cartridge assembly 30 snaps onto the breech plug 32 and the assembly may be carried by the knob 34; and (3) the knob 34 serves as a handle to insert and fasten the assembly to the tube pressure vessel with the extraction tube communicating with an outlet aligned with its axis and an inlet for the space between the internal walls of the pressure vessel and the exterior of the extraction cartridge and for the interior of the extraction cartridge being provided through a groove circumscribing the assembly inside the pressure vessel.

With this arrangement the extraction cartridge assembly 30 may be easily sealed in the pressure vessel 24 by threading the breech plug 32 into it and removed by unthreading the breech plug 32 and lifting by the knob 34. The extraction cartridge assembly 30 contains a hollow interior, an inlet and an outlet so that a sample to be extracted may be placed in the hollow interior and supercritical fluid passed through the inlet, the hollow interior and to the outlet to a collector. The extraction cartridge assembly 30 serves as an extraction chamber or tube, the pressure vessel 24 serves as an extraction vessel and the heating block 22 serves as an oven as these terms are commonly used in the prior art.

In the preferred embodiment, the knob 34 is of a low heat conductivity material and it should include in all embodiments at least a heat insulative thermal barrier located to reduce heating of the handle portion of the knob 34. It extends outside of the pressure vessel 24 and is adapted to aid in the sealing of the pressure vessel 24 and the breech plug 32 together so that the extraction cartridge assembly 30 is within the pressure vessel 24 for maintaining it at the appropriate temperature and the knob 34 is outside the pressure vessel 24 so as to remain cool enough to handle.

Although in the preferred embodiment the knob 34 is a heat insulative material, it only needs to be insulated against heat conducted from the interior of the pressure vessel 24 and this may also be done by a thermal barrier separating the pressure vessel 24 from the knob 34 such as an insulative disc having a width of at least 1 millimeter and extending across the cross-section of the knob 34 to the extent of at least 80 percent of the cross-section so as to effectively block any considerable amount of transfer of heat between the cartridge and the knob 34.

It should have a heat conductivity no greater than 0.05 calories/cm. sec. degree C. at 30 degrees Centigrade.

The extraction cartridge has an opening which permits some supercritical fluid to enter the pressure vessel 24 to follow one path passing into the extraction tube 5 and out through an outlet of the extraction tube into a conduit leading to a collector. Other supercritical fluid follows a second path around the outside of the cartridge to remove contaminants from the pressure vessel 24, equalize pressure and flow from another outlet. One of the inlet and outlet of the extraction cartridge assembly 30 enters along the central axis of the extraction cartridge assembly 30 and the other from the side to permit rotation of parts with respect to each other during seating of the pressure vessel 24 and yet permit communication of the extraction cartridge assembly 30 with the fluid source and with the collector. To reduce wasted heat and fluid, the space between the outside of the cartridge and the inside walls of the pressure vessel 24 is only large enough to accommodate the flow of purging fluid and to equalize pressure between the inside and outside of the cartridge. The volume between the outside of the cartridge and the inside of the pressure vessel 24 is less than 10 cubic centimeters.

In the preferred embodiment, the inlet opens into an annular space between the internal wall of the pressure vessel 24 and the cartridge and plug assembly 26. The fluid follows two paths from the annular space, both of which include an annular manifold with narrow holes and a passageway that communicates with the recess in the breech plug 32. One path opens into the extraction cartridge assembly 30. The other passes along the narrow space outside the extraction cartridge assembly 30. Thus, supercritical fluid enters the extraction tube through a labrythian like path and at the same time passes outside the extraction tube so that the pressure inside the extraction tube is always substantially the same as that inside the pressure vessel 24. Because the pressures are substantially the same, the tube itself may be formed of relatively inexpensive plastics notwithstanding that a high pressure is desirable for extraction from the sample within the extraction tube.

The pressure vessel 24 is generally formed of strong material such as metal and is shaped as a container with an open top, an inlet opening and two outlet openings. The inlet opening is sized to receive an inlet fitting 42, the inlet fitting 42 being shown in FIG. 1, connected in series with check valve 60A to corresponding heat exchanger 40. Each of the two outlet openings are sized to receive a different one of a corresponding purge valve fitting 44, and a corresponding extractant fluid fitting 46. With these fittings, the pressure vessel 24 is able to receive the cartridge and plug assembly 26 in its open end and permit communication between the cartridge and the extractant fluid fittings such as shown at 46. The inlet fittings such as shown at 42 and purge valve fitting, such as 44, permit communication with the inside of the pressure vessel 24.

To control the flow of fluids to and from the pressure vessel and fluid-extraction assembly 18, the valve system 14 includes an extractant valve 50, a purge fluid valve 52 and an extracting fluid valve 54.

To introduce extracting fluid into the pressure-vessel and fluid-extraction assembly 18, the extracting fluid valve 54 communicates with one branch of the tee joint 20 through tube 56 and with one end of the heat exchanger 40 through tube 58, the other end of the heat exchanger 40 communicating with the inlet fitting 42 through tube 60, check valve 60A and tube 60B. With these connections, the extracting fluid valve 54 controls the flow of fluid from the pumping system 12 through the heat exchanger 40 and the pressure vessel 24 through the inlet fitting 42.

To remove purge fluid from the pressure vessel 24, the purge fluid valve 52 communicates at one port with the purge valve fitting 44 through tube 62 and through its other port and tube 64 with the collector system 16 or with a vent (not shown) to remove fluid containing contaminants from the exterior of fluid extraction cartridge assembly 30 and the interior of the pressure vessel 24.

To remove extractant from the extraction cartridge assembly 30, the extractant valve 50 communicates at one of its ports through tube 66 with the extractant fluid fitting 46 and through its other port with the collector system 16 through tube 68 for the collecting of the extracted material, sometimes referred to as analyte or extractant, from the sample within the pressure-vessel and fluid-extraction assembly 18.

For convenience, the valves 52 and 54 are mounted to be operated by a single manual control knob 70. To supply fluid to the valve system 17: (1) the tube 56 carries pressurized fluid from the pumping system 12 to tee joint 20; (2) tube 76 is connected to one arm of tee joint 20 to carry pressurized fluid to another extractor unit not shown on FIG. 1; and (3) the remaining arm of tee joint 20 is connected through the tube 56 to an inlet fitting 74 of extracting fluid valve 54. The valves 50, 52 and 54 are, in the preferred embodiment, SSi type 02-0120.

The extracting fluid valve 54 has a rotary control shaft 80 that is rotated to open and close its internal port. This shaft is operated by hand control knob 70 and carries spur gear 82 pinned to the control shaft 80. Spur gear 84, which is pinned to control shaft 107 of purge fluid valve 52, meshes with spur gear 82 so that when control knob 70 is rotated clockwise, extracting fluid valve 54 is closed, but since the control shaft 107 of purge fluid valve 52 is geared to turn in the opposite direction, the clockwise rotation of knob 70 opens purge fluid valve 52.

The relative locations of the two gears on the two shafts are such that, in the first (clockwise) position of the knob 70, extracting valve 54 is shut and purge fluid valve 52 is open. Turning the control knob 70 counterclockwise 130 degrees from this first position opens extracting fluid valve 54 while allowing purge fluid valve 52 to remain open. Thus, both valves are open when the knob 70 is rotated 130 degrees counterclockwise from the first position. When the knob 70 is rotated 260 degrees counterclockwise from the first position, extraction fluid valve 54 is open and purge fluid valve 52 is shut. Thus, there are three definable positions for control knob 70: (1) clockwise with valve 54 shut and valve 52 open; (2) mid position with both valves open; and (3) full counterclockwise with valve 54 open and valve 52 shut.

The extractant valve 50 includes an inlet fitting 120, outlet fitting 122, manual control knob 132 and control shaft 126. The rotary control shaft 126 is attached to control knob 132. When the valve 50 is opened by turning the control knob 132 counterclockwise from its closed position, fluid flows from the extraction cartridge assembly 30, through the fluid fitting 46, conduit 66, valve inlet fitting 120, outlet fitting 122, through tube 68 and into the collection system 16.

The collector system 16 includes a purge coupling 90, a purge fluid collector 92, an extractant coupling 94, an analyzing instrument 96, and an extractant fluid collector 98. The purge fluid flowing through the valve 52, flows through purge coupling 90 into the capillary tube 110 and from there into the collector 92 where it flows into a solvent 100. Similarly, the extractant flowing through valve 50 flows through tube 68 to the coupling 94 and from there to the capillary tube 128 and collector 98 which contains an appropriate solvent 104 in the preferred embodiment.

The analytical instrument 96 may be coupled to the capillary tube 128 through an optical coupling 102 in a manner known in the art. The optical coupling 102 is a photodetector and light source on opposite sides of a portion of the capillary tube 128, which portion has been modified to pass light. This instrument 96 monitors extractant and may provide an indication of its passing into the collector 98 and information about its light absorbance. Other analytical instruments may also be used to identify or indicate other characteristics of the extractant.

Figure 2:
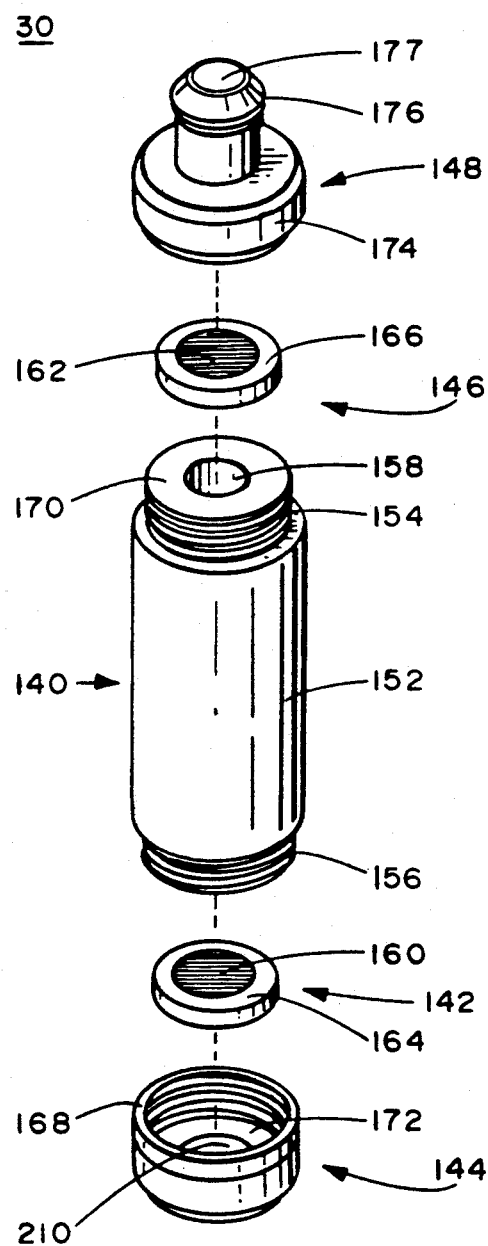
FIG. 2 is an exploded perspective view of an extraction cartridge used in the embodiment of FIG. 1 according to the invention.

In FIG. 2, there is shown an exploded perspective view of the supercritical fluid extraction cartridge assembly 30, having a substantially cylindrical tubular body portion 140, a bottom porous means 142 such as a filter, frit or other means for confining sample, a bottom cap 144, and a top porous means 146 such as a filter, frit, or means for confining sample and a top cap 148.

In one embodiment, the tubular body portion 140 is a cylindrical steel tube adapted to hold within it the sample 134 (FIG. 1) having shoulders on each end with reduced diameter externally threaded top and bottom end portions 154 and 156. A central opening 158 passes along its axis for receiving sample. However, the tube may take other shapes and be formed of other suitable materials.

To confine the sample, the bottom and top porous means 142 and 146 each include stainless steel porous frit members 160 and 162 held within different ones of two sealing rings 164 and 166 respectively. The frit members 160 and 162 have the same diameter and are arranged to be aligned with the central opening 158 and the sealing rings 164 and 166 have the same internal and external diameter as the end portions 154 and 156 of the tube 152 to lie flat over the tubular body portion 140 with the frit members 160 and 162 closing their ends.

The sealing rings 164 and 166 are preferably made of Teflon or Kel-F (trademarks of E. I. DuPont de Nemours Co., Wilmington, Del., United States of America for tetrafluoroethylene and other fluorocarbon plastics). The top and bottom caps 144 and 148 include internal threads such as the threads 168 in the bottom cap 144 that engage with corresponding external threaded end portions 156 and 154 of the tube 152 to hold the top and bottom cap portions 142 and 144 in place.

The bottom cap 144 is sized so that when threaded against the shoulder or the body portion 140, it sealingly forces the ring 164 against the bottom face of the tubular body portion 140 to form a seal and hold the frit member 160 in place. Similarly, the top cap 148 is sized to compress the ring 166 against an annular face 170 of the top end portion 154 of the tubular body portion 140 to form a seal. The bottom cap 144 has an inwardly turned annular flange 172 for engaging the ring 164 with a central opening 210 for an outlet fitting and a similar flange is in the top cap 142. Within the flanges are corresponding circular apertures substantially the same size as the porous means 142 and 146 and of the central opening 158 and aligned therewith for the passage of fluid.

The upper cap 148 includes lateral sides 174 having internal threads for compressing the frit member 162 in place and an engaging nipple 176 having an open end 177. The extraction tube 152 may be machined of 303 stainless steel for a permanent cartridge or molded of polyphenylene sulfide, polyetherimide or polyethersulfone plastic for a disposable cartridge. This cartridge has an internal volume for sample of 2.5 cubic centimeters in the preferred embodiment, but may be as large as 1000 cubic centimeters. The top and bottom caps 144 and 148 may be machined from polyetherketone plastic for a permanent cartridge or molded of polyetherimide or polyethersulfone plastic for a disposable cartridge.

Figure 3:
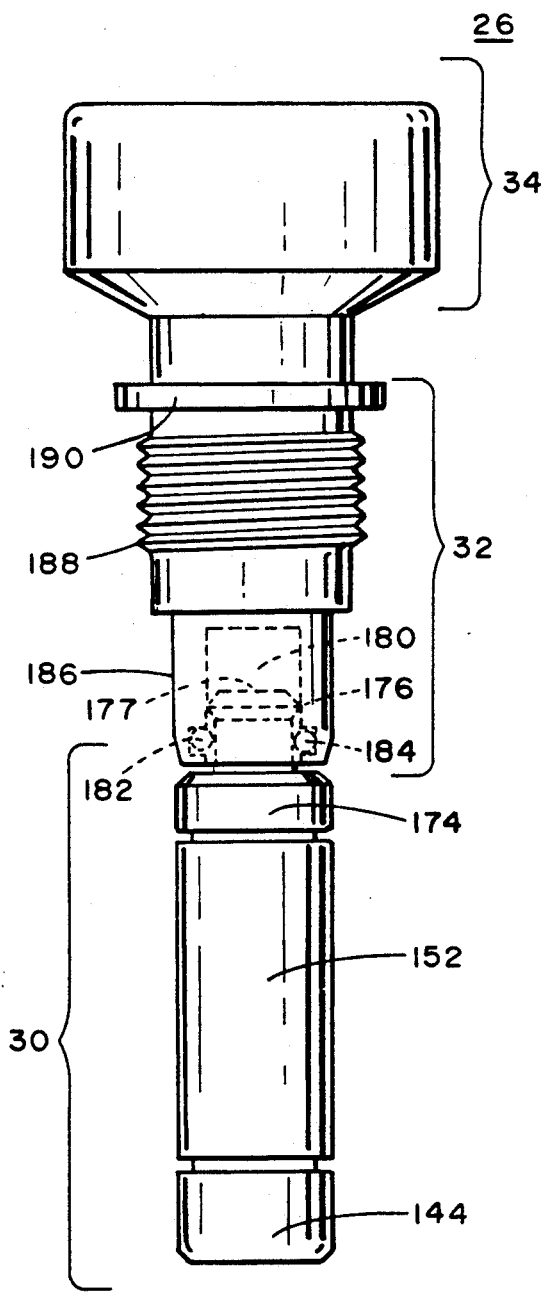
FIG. 3 is an elevational view of the extraction cartridge of FIG. 2 clipped into a breech plug used in the embodiment of FIG. 1.

In FIG. 3, there is shown an assembled cartridge and plug assembly 26 having a breech plug 32, an extraction cartridge assembly 30 and a knob 34.

The breech plug 32 is made of high strength, corrosion resistant, stainless steel (Nitronic 50) and includes cylindrical recess 180, sealing surface 186, engaging thread 188 and annular stop flange 190. The cylindrical recess 180 is positioned to receive engaging nipple 176 on one side and the knob 34 on the other with the external threads 188 between them for forming a closure with the pressure vessel. Near the outer end of the recess 180 is located a retaining groove 182. Within this groove 182 is located a garter spring 184.

The garter spring 184 is a helical coil of stainless steel wire bent into the shape of a circle and welded closed at the ends to form a torus. The turns of the helix are inclined to the helix axis so that they deflect rather than buckle when a circular member of outside diameter greater than the inside diameter of the torus is pressed through the center of the torus while the outside diameter of the torus is constrained by means such as the groove 182. Therefore, upon pressing the extraction cartridge assembly 30 into the recess 180 so that the major diameter of its engaging nipple 176 pops past the garter spring 184, the extraction cartridge assembly 30 is retained in breech plug 32. The strength of retention depends upon the strength of the garter spring 184. The garter spring 184 is chosen so that the cartridge is retained against gravity and other relatively light forces but still is easy to remove manually by pulling it from the breech plug 32.

The knob 34 is fastened to the top of breech plug 32 by any conventional means. In the preferred embodiment, knob 34 is fabricated of temperature-resistant insulating material, such as phenolic plastic and fastened in place.

Figure 4:
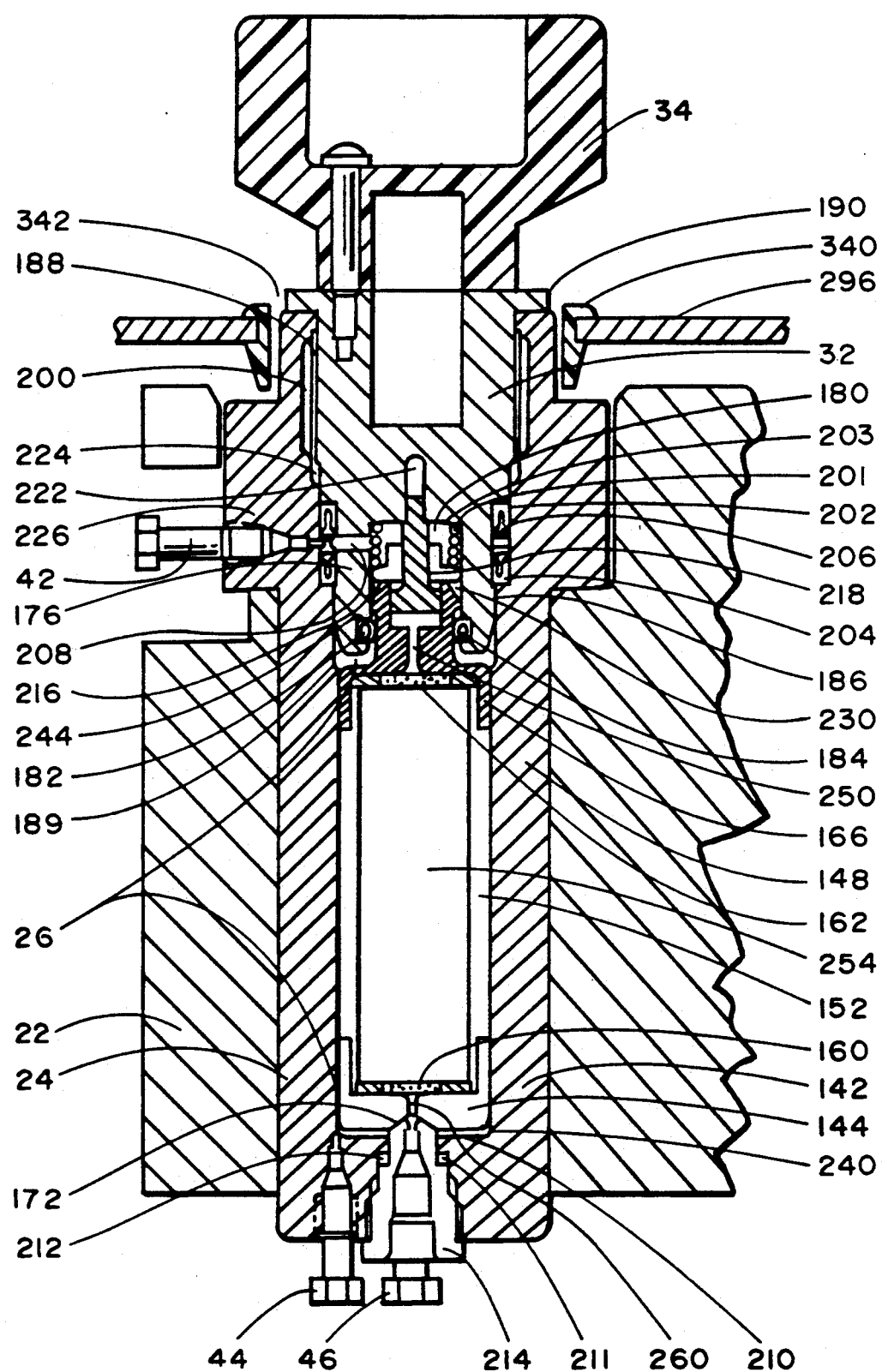
FIG. 4 is a fragmentary sectional view of the extraction cartridge, breech plug pressure vessel and heating block.

In FIG. 4, there is shown a sectional view of the clipped-together extraction cartridge 26, knob 34 and breech plug 32 replaceably installed in pressure vessel 24 which in turn has previously been permanently force fit into heating block 22. The pressure vessel 24 is fabricated of type 303 stainless steel for good machinability and corrosion resistance and has within it a cylindrical central opening sized to receive the extraction cartridge 26, two openings for outlet fittings in its bottom end, an opening in its cylindrical side wall to receive an inlet fitting and an open top with internal threads sized to engage the external threads 188 of the breech plug 32. The heating block 22 is fabricated from aluminum for good thermal conductivity and includes a cylindrical opening sized to tightly receive the pressure vessel 24.

The breech plug 32 and the extraction cartridge assembly 30 are a slip fit within the pressure vessel 24. External threads 188 on breech plug 32 engage in internal threads 200 within pressure vessel 24.

An annular self-acting high pressure seal 202 cooperates with a sealing surface 186 to seal high pressure supercritical fluid from the atmosphere and an annular low pressure seal 204 spaced from the annular high pressure seal 202 prevents contaminated supercritical fluid in the space between the interior of the pressure vessel 24 and the exterior of the extraction cartridge assembly 30 from getting back to the supercritical fluid supply. These two annular seals 202 and 204 form between them a torroidal inlet chamber into which the outlet of the fluid inlet 42 extends to introduce fluid. Contamination may arise from fingerprints or other foreign material on the outside wall of extraction cartridge assembly 30 and the low pressure seal 204 protects against this contamination. Seals 202 and 204 are Bal-Seal type 504MB-118-GFP.

Supercritical fluid is supplied to fluid inlet 42 and circulates in the annular space between high pressure seal 202 and low pressure seal 204, and then follows two paths into the pressure vessel 24 and extraction: one for purging and one for extraction. An annular spacer 206 within the torroidal opening between seals 202 and 204 has an hour-glass shaped cross section with radial holes through it and distributes incoming supercritical fluid from the inlet of fitting 42 to the opposite side of the spacer 206 from which it flows to passageway 208 drilled in breech plug 32.

Because the passageway 208 extends radially from the recess 180 in the breech plug 32 to the annular ring, it provides an open path for fluid between the two regardless of the orientation of passageway 208. The passageway 208 opens at an uncontrolled angular location with respect to the inlet fixture 42 (inner side). Fluid flows from one side of the inwardly curved portion of the hour glass shaped spacer 206 that communicates with the outlet of fitting 42 to the other side of the inwardly curved portion and from there to the passageway 208.

When the cartridge and plug assembly 26 shown in FIG. 3 are inserted into the pressure vessel 24 as shown in FIG. 4, the knob 34 is rotated and the external threads 188 of the breech plug 32 which form an eight thread per inch connector engage internal threads 200 in the pressure vessel 24, screwing the breech plug 32 and attached cartridge and plug assembly 26 down into the pressure vessel 24. When conical recess 210 in the bottom cap 144 formed by flange 172 reaches the external conical tip 212 of fitting adapter 214, the cartridge assembly 26 is prevented from moving further down.

Screwing the breech plug 32 in further after the cartridge and plug assembly 26 has bottomed causes the upper flat annular surface of fitting nipple 176 to bear upon the flat lower surface of a hat-shaped washer 216. At this time, the hat-shaped washer 216 is residing against the upper surface of the head of a shoulder screw 218 which is threaded into cylindrical hole 222 in breech plug 32.

Further screwing of the breech plug 32 into the pressure vessel 24 causes the nipple to lift the washer 216 off of the screw head and compress a coil spring 201 between annular surface 203 and the ridge of the washer 216. Continued screwing of the breech plug 32 into the pressure vessel 24 causes annular flange 190 of breech plug 32 to bear upon the upper surface of the pressure vessel 24. This provides a limit stop with the coil spring 201 compressed, as shown in FIG. 4.

The force of the compression spring 201 is enough to provide a low pressure seal between the hat-shaped washer 216 and the upper annular surface 203 of the fitting nipple 172. More importantly, this force also provides a low pressure seal on the mating conical surfaces of the recess 210 of lower cap 144 and the external conical tip 212 of the fitting adapter 214 compressing washer 211.

The sealing surface 186 acts as a pilot during the initial part of insertion to insure that threads 188 do not get cross-threaded. A taper 189 at the end of the cylindrical sealing surface 186 pilots the breech plug 32 past seals 202 and 204 so that they are not damaged during insertion of the breech plug 32.

The locations of recess 224, passageway 208, high pressure seal 202 and the engaging threads 188 and 200 are chosen such that if the breech plug 32 is inadvertently removed when the interior of the pressure vessel 24 is pressurized, fluid within the pressure vessel 24 leaks past high pressure seal 202 and runs up the flights of the engaging screw threads 188 and 200, and depressurizes the system, while there is still adequate screw engagement to ensure safety at the maximum rated operating pressure. The maximum rated operating pressure of the embodiment shown in FIG. 4 is 10,000 psi. The maximum operating temperature is 150 degrees Centigrade. The equipment need not be designed for operating temperatures above 300 degrees Centigrade and pressure above 30,000 pounds per square inch.

After the breech plug 32 and the cartridge and plug assembly 26 are assembled into the pressure vessel 24 as described above, but before an extraction, the space between the cartridge and plug assembly 26 and the pressure vessel 24 is purged of contaminants. During such a purge or cleaning cycle supercritical fluid enters fitting 42, is distributed by spacer ring 206 and goes through passageway 208. It passes between the outer diameter of hat-shaped washer 216 and the inside cylindrical diameter 230 of the recess within breech plug 32. Fluid then continues down and passes the annular space between the outside diameter of engaging nipple 176 and inside diameter 230 of the recess 180 in breech plug 32. The fluid passes garter spring 184 and circulates with even circumferential distribution around the outside of top cap 148, the extraction tube 152, and the bottom cap 144. The flow is collected in the annular space below the bottom cap 144 and above the bottom 240 of pressure vessel 24 and exits through vent discharge fitting 44, carrying contaminants with it.

Contaminated fluid between the exterior of extraction cartridge 26 and the interior of high pressure vessel 24 does not make its way into the interior of the extraction vessel. Low pressure seal 204 prevents contaminated fluid from reaching passageway 208. A labyrinth seal consisting of the narrow gaps between the major diameter of fitting nipple 176 and the inside diameter 230 of recess 180, and between inside diameter 230 and the outside diameter of the hat-shaped washer 216, prevents contaminants from reaching the space above the hat-shaped washer by diffusion.

During a purge or cleaning cycle there is downward flow of supercritical fluid through these gaps, and since the gaps are small, this downward fluid flow prevents eddies of contaminated fluid from passing up through the gaps. These gaps are only a few thousandths of an inch. Because the top of nipple 176 and the conical recess 172 at the bottom of the extraction cartridge are sealed by spring pressure, contamination cannot enter in these ways.

For extraction, supercritical fluid entering fitting 42 is distributed in the space occupied by spacer ring 206, flows through passageway 208 and flows down the few thousandths of an inch radial gap between the shoulder of shoulder screw 226 and the inside diameter of washer 216. The fluid continues to flow down and flows through passageway 250, porous frit 160 and into extraction volume 254 were it passes through material to be extracted. Extraction volume 254 is shown sized in FIG. 4 for a 2.5 cubic centimeter volume to receive sample. After passing the extraction volume fluid it is then exhausted for sample collection through frit 160, passageway 260, fitting adapter 214 and out through fitting 46.

All tubing, except tubing designated as capillary tubing, in this disclosure is 300 series stainless steel with an outside diameter of 1/16 inch and inside diameter 0.02 inch.

In operation after assembly, the fluid flow associated directly with valve 54 (FIG. 1) exiting its port 114 flows through tube 58 through heat exchanger 40, which is formed by coiling a contiguous segment of tubing into a helix, through heat exchanger 60A and tube 60B and to entrance fitting 42 of pressure vessel 24. Heat exchanger 40 actually resides in a longitudinal bore through heating block 22 so that the heat exchanger is at the same temperature as pressure vessel 24 and extraction tube 30. This preheats any fluid flowing into inlet fitting 42 to essentially the same temperature as the extraction cartridge assembly 30. This temperature is above the critical temperature for the fluid. Assuming that the pump 12 is set to produce a constant fluid pressure greater than the critical pressure, fluid entering the pressure vessel 24 will be a supercritical fluid.

Check valve 60A prevents backflow of supercritical fluid out of the pressure vessel 24 and extraction cartridge 26 of a first channel of a dual channel supercritical extraction system if there is a momentary drop in pressure of the supercritical fluid at the location of tee 20. Such a pressure fluctuation could occur if the second channel of a dual channel extraction system is suddenly purged while the first channel is extracting. Each channel requires such a check valve.

During a purge cycle, contaminated supercritical fluid leaves fitting 44, flows through tube 66, enters inlet fitting 116 of valve 52. Then it exits outlet fitting 118 and passes through tube 64 to coupling 90. Coupling 90 couples quartz capillary tube 110 so that contaminated purge gas exits through it. The bore of the capillary tube is small enough, such as 75 micrometers, and its length long enough, on the order of a few inches, to provide enough fluid resistance to limit the flow to a convenient rate: for example 5 milliliters per minute with respect to displacement of pump 12, at a pressure of 3,000 psi. Pump 12 is a constant pressure pump so this fluid flow does not affect the pressure within pressure vessel 24 once the flow stabilizes.

The outer end of capillary 110 may be immersed a test tube 92 containing an appropriate solvent 100 such as isopropyl alcohol to serve as a collector. Bubbles through this solvent indicate proper flow and the solvent tends to prevent the end of the capillary tube 110 from being plugged by the exhausted contaminants. A solvent is chosen in a manner known is the art to dissolve contaminants so the end of the capillary tube 110 does not plug and so the solvent may later be analyzed if desired to determine whether there was any contaminants on the exterior of the extraction cartridge.

During an extraction cycle, extractant exits fitting 46 on pressure vessel 24 and passes through tube 66. This tubing extends to inlet fitting 120 of valve 50 which has rotary control shaft 126 attached to control knob 132. When the valve is opened by turning it counterclockwise from its closed position, fluid exits from its fitting 122, through tube 68 to fitting 94. Fitting 94 couples to quartz capillary tube 128.

Capillary tube 128 has a small enough bore, such as 50 micrometers, and a long enough length, on the order of several inches, to produce a flow rate, relative to the displacement of constant pressure pump 12, of a convenient amount. For example, this may be two milliliters per minute. The end of capillary 128 dips into solvent 104 in test tube 98.

Isopropyl alcohol is under some circumstances used for solvent 104. This solvent 104 must be good solvent for the extractant since it must trap the extractant by dissolving it from the gas bubbling through it and must prevent plugging at the end of the capillary tube 128.

The solvent 104 is removed after extraction and is analyzed to determine the composition and amount of the extractant. Because of the pressure and temperature drop along the length of capillary 128 (and also capillary 110) fluid entering the capillary as a supercritical fluid (or a liquid if fitting 90 or fitting 94 is not heated) changes to a gas by the time it reaches the far end where it dips into the solvent which is at room temperature.

In FIGS. 5-9, there are shown, in five orthographic views, the physical structure of a preferred embodiment of an extraction system 10 dual station supercritical extraction apparatus 10. For simplicity one station of the dual apparatus is shown with its complete fluid connections and only this one is described in detail. The second extraction station is substantially identical to the first. The fluidic connections in FIGS. 5-9 correspond to the connections in FIG. 1. The components described and numbered in FIG. 1 carry like identifying numbers in FIGS. 5-9. A corresponding second extraction station components in FIG. 5 carry corresponding numbers modified with the addition of a prime (') sign.

Figure 5:
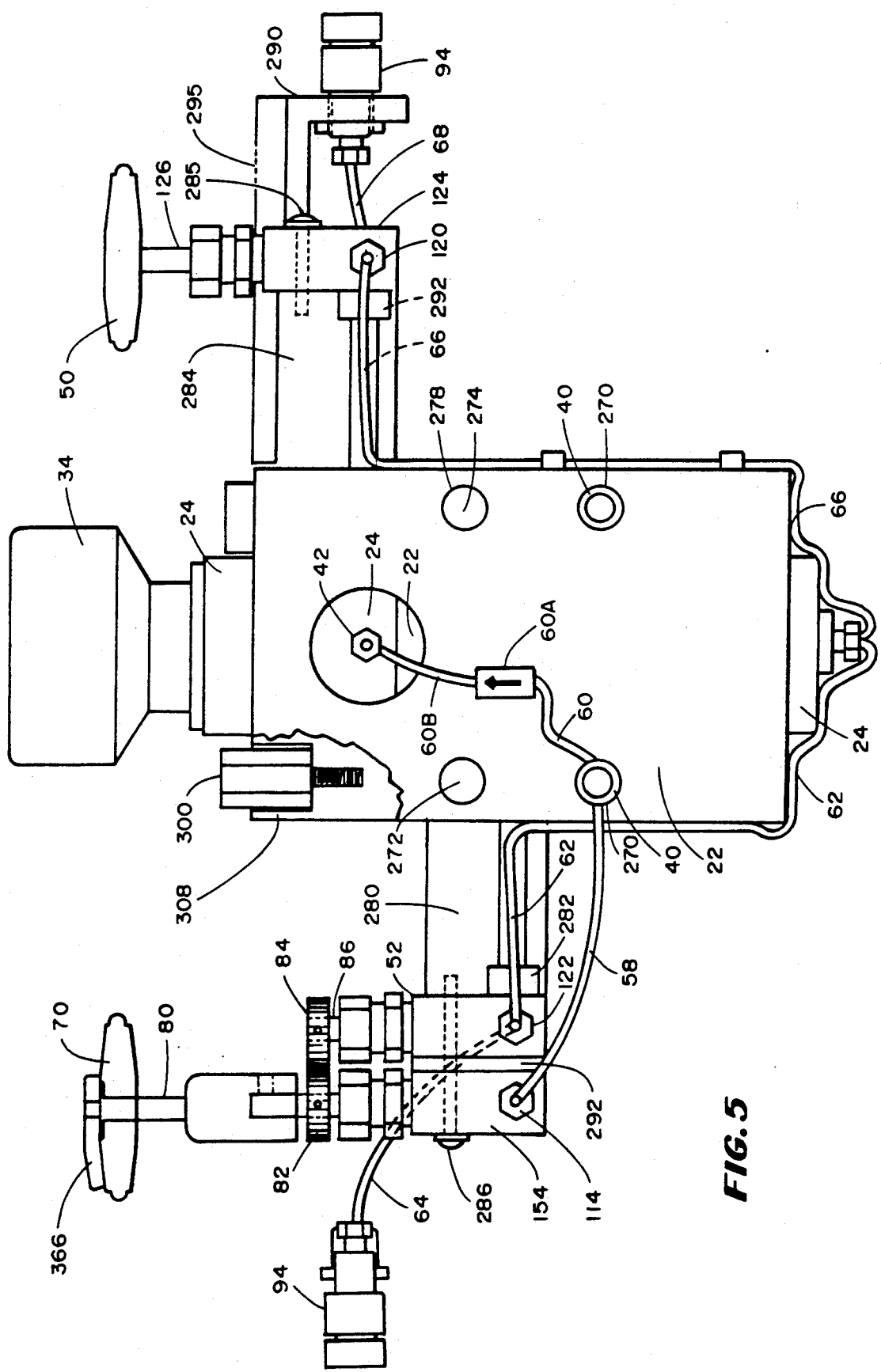
FIGS. 5-8 are four-view orthographic projections showing the major working parts of a dual supercritical fluid extractor of FIGS. 1-4, with FIG. 5 being a front elevational view, FIG. 6 being a top view, FIG. 7 being a left side elevational view, and FIG. 8 being a right side elevational view.
Figure 6:
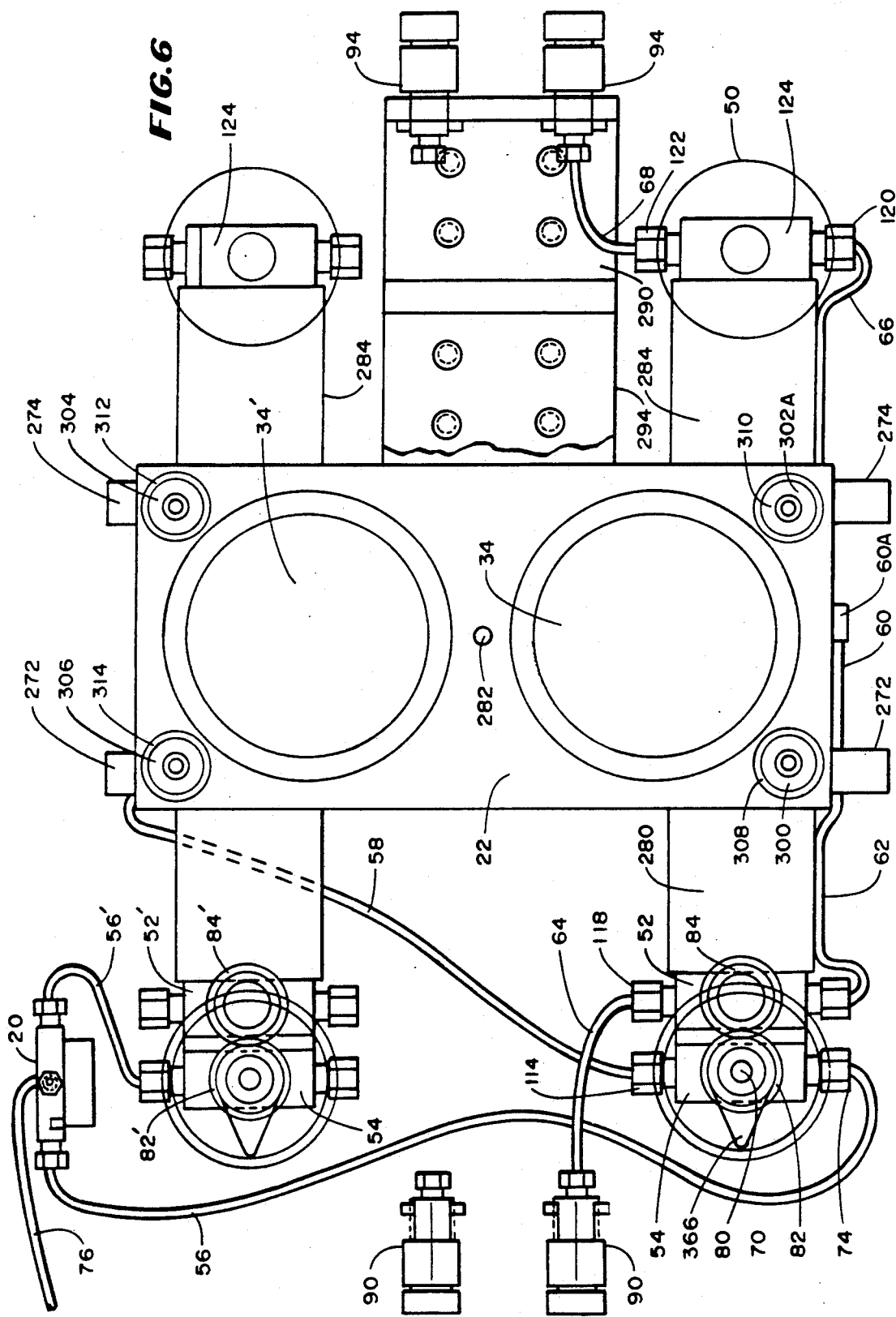
Figure 7:
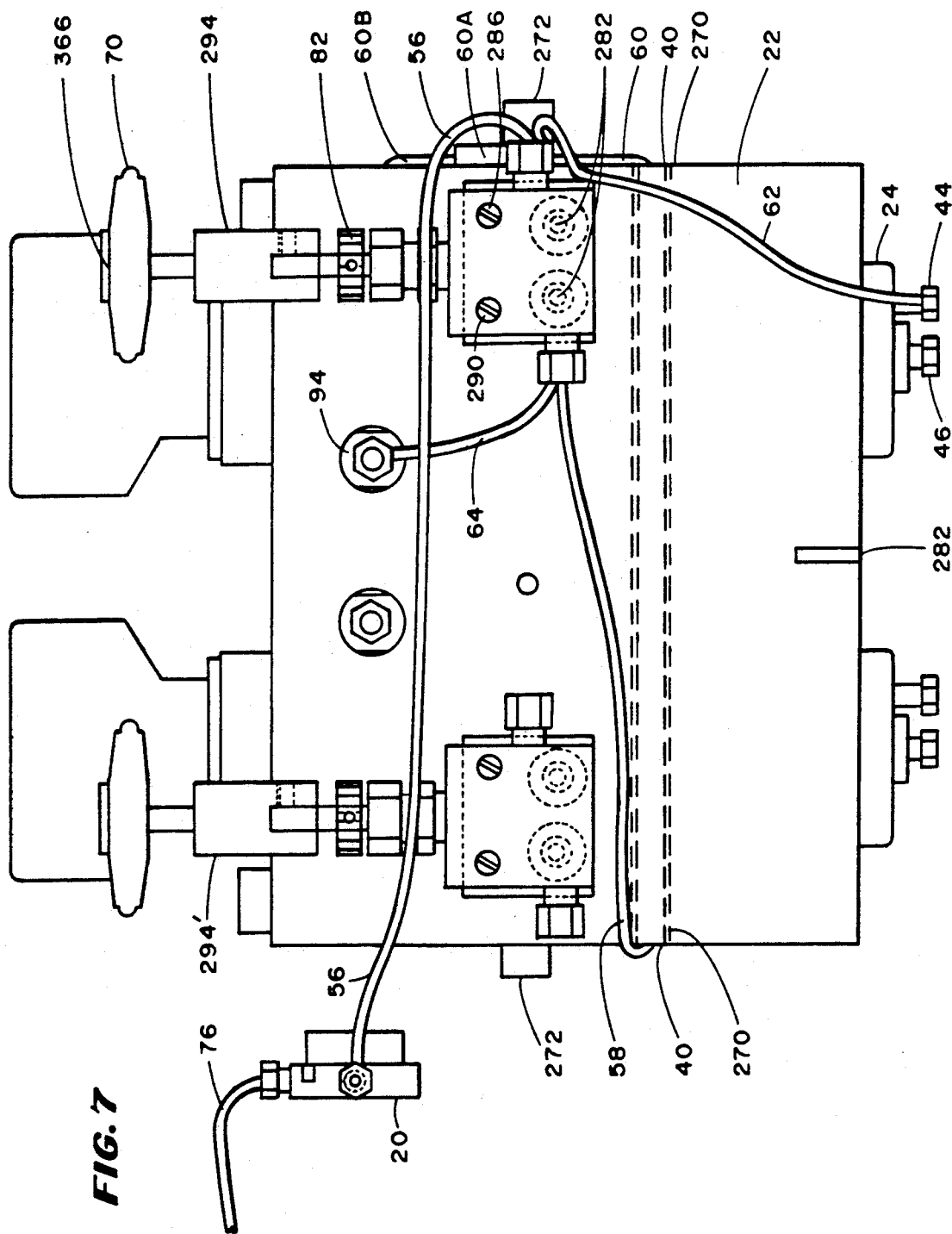
Figure 8:
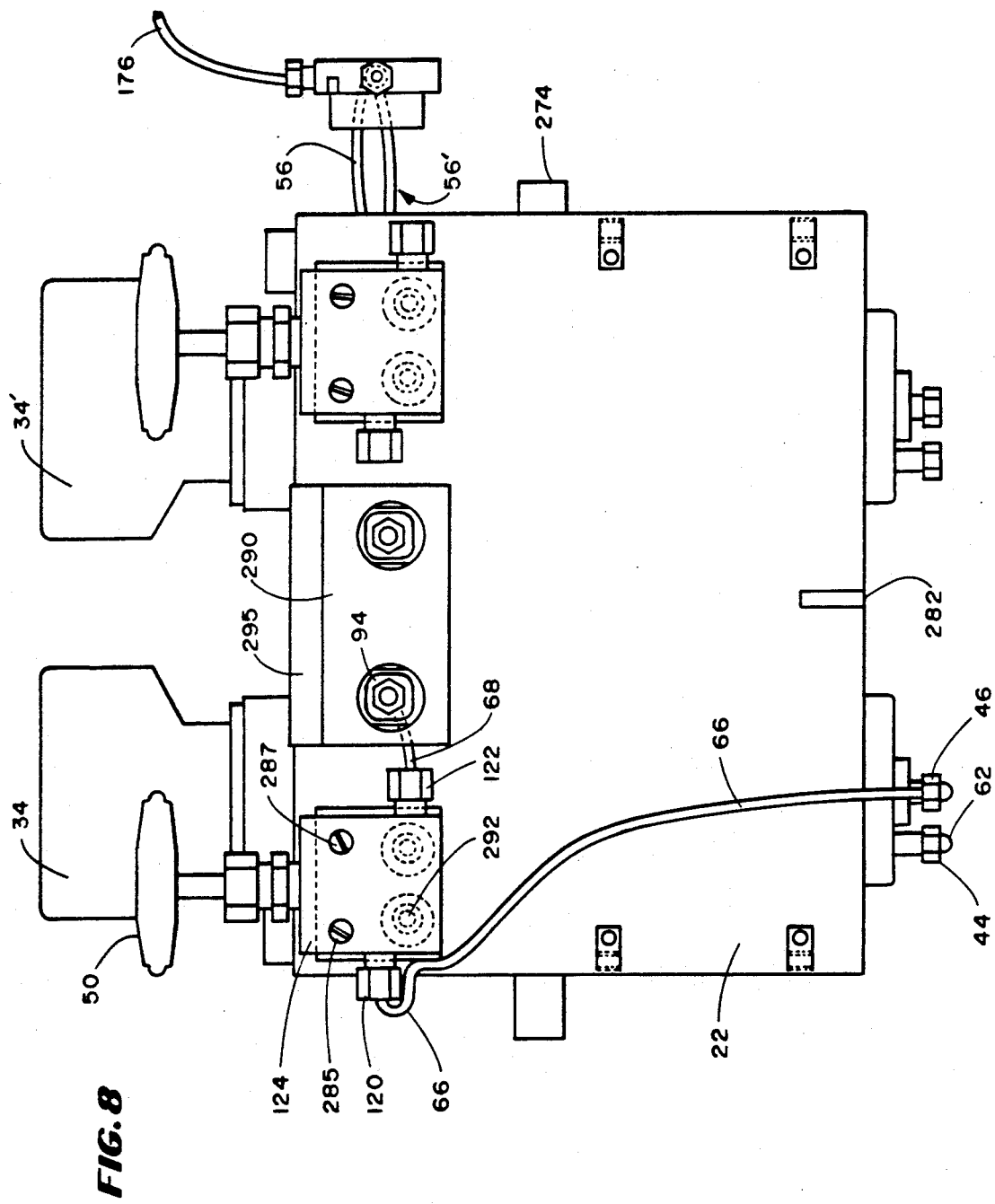
Figure 9:
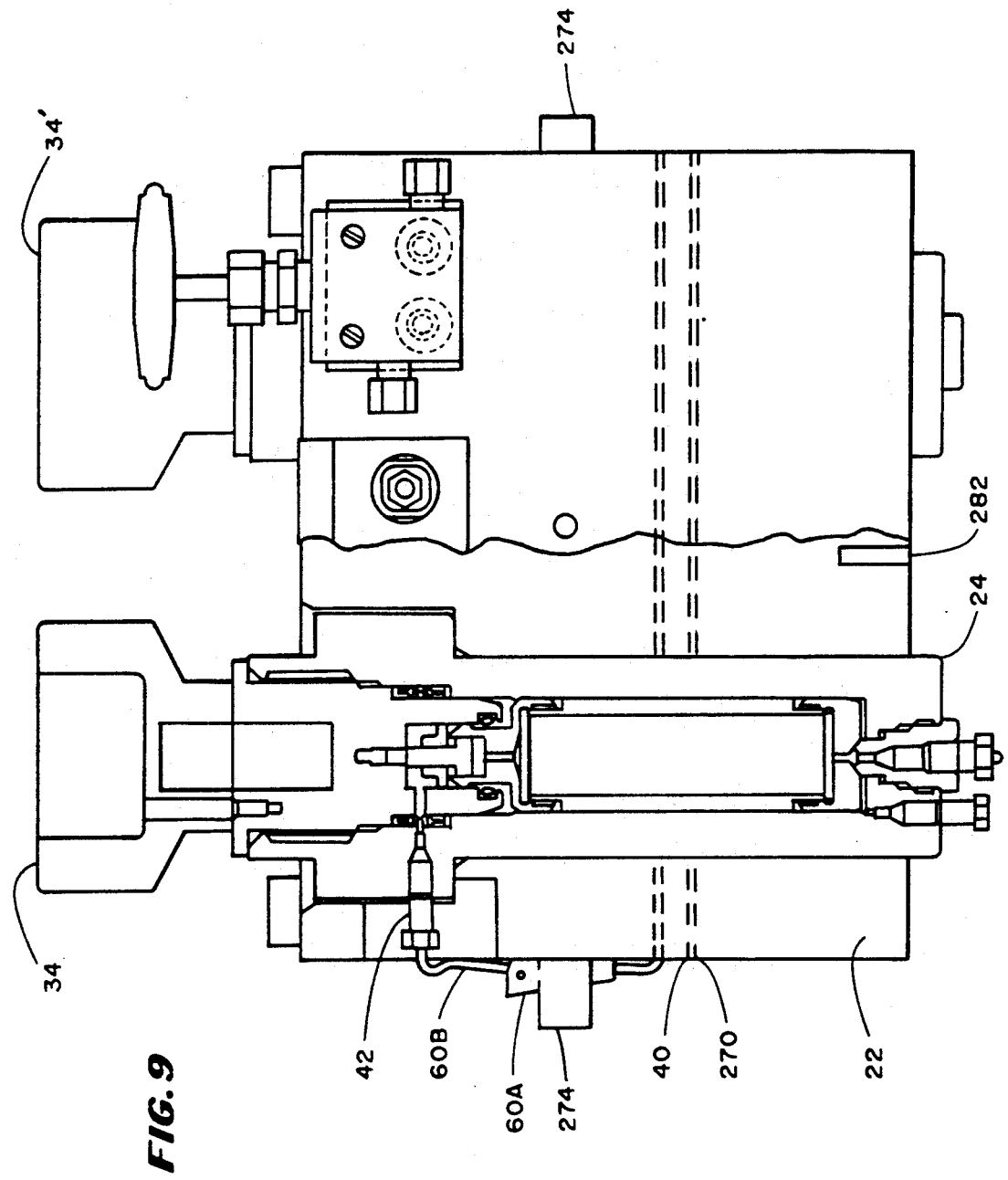
FIG. 9 is a partly sectional, partly broken away, right elevational fragmentary view of the supercritical extractor of FIGS. 5-8.

As best shown in FIG. 5, the heat exchanger 40 is located within bore 270 in heating block 22. The tube 58 enters this bore at one end, is coiled in a helix throughout the length of bore 270, and exits the other end as tube 60 which communicates with inlet fitting 42 of pressure vessel 24 within heating block 22. Tubular heating elements 272 and 274 are located within bores 276 and 278 and extend therewith throughout the length of heating block 22. They protrude from both ends of heating block 22 as shown in FIG. 6. In the preferred embodiment, these heating elements have a total heating power of 800 watts; 400 watts each.

Aluminum support block 280 is fastened to heating block 22 by cap screws 282 recessed within support block 280. Valves 54 and 52 are fastened to support block 280 by screws 286 and 290, and the valves are separated by spacer 292. Support block 280 is thermally conductive and heats valve 52 to a temperature near that of the heating block 22.

Aluminum support block 284 is held to heating block 22 by cap screws 292 recessed within support block 284. The body of valve 124 is screwed to support block 284 with screws 285 and 287. The high thermal conductivity of support block 284 heats valve 124 to approximately the temperature of heating block 288. The tube 68 leads from valve 124 to outlet fitting 94. Outlet fitting 94 is heated to a temperature near that of support block 22 because it is mounted to aluminum angle 290 which in turn is mounted to aluminum plate 295 that is fastened to support block 294 shown in top view in FIG. 6. Support block 294 is screwed (fastening not shown) to heating block 22. Since support block 294, plate 295 and angle 290 are made of thermally conductive aluminum, heat from heating block 22 is efficiently conducted to fitting 94.

Tubes 60, 62 and 66 are routed in contact with heating block 22 or in contact with thermally conductive supporting members in contact with heating block 22. This keeps the tube and their contents sufficiently hot so that dissolved sample contents or contaminants do not condense or precipitate from solution in the supercritical fluid. The tube 68 is kept hot because of the location of the insulation to be described in FIGS. 10–14.

FIGS. 10–13 are a four-view orthographic projection of the outside cabinet enclosing the dual extraction system illustrated in FIGS. 5–9 with FIGS. 10 and 11 being a front elevational broken away view and a plan broken away view respectively showing the dual extractor unit of FIGS. 5–9 mounted under cabinet top 296. As shown in FIG. 10, dual extraction unit is separated from the top of the cabinet 296 by the four tubular phenolic spacers 300 and 302, 304 and 306 (FIG. 6) two of which are shown at 300 and 302 in FIG. 10, which spacers extend into recesses 308, 310, 312 and 314 (FIG. 6) in the heater block 22 (FIGS. 5–9). Stainless steel screws 320, 322, 324 and 326 extend through the bores of the tubular spacers 300, 302, 304 and 306 (FIG. 6) into tapped holes 330, 332, 334 and 336 (FIG. 6) in heater block 22.

The stainless steel material of the screws 320, 322, 324 and 326 is a poor conductor of heat, and the phenolic spacers 300, 302, 304 and 306 (FIG. 6) are even poorer conductor of heat; thus thermally isolating the heating block 22, pressure vessel 24, breech plug 32, the valves, and other heated components from the cabinet cover 296.

Figure 13:
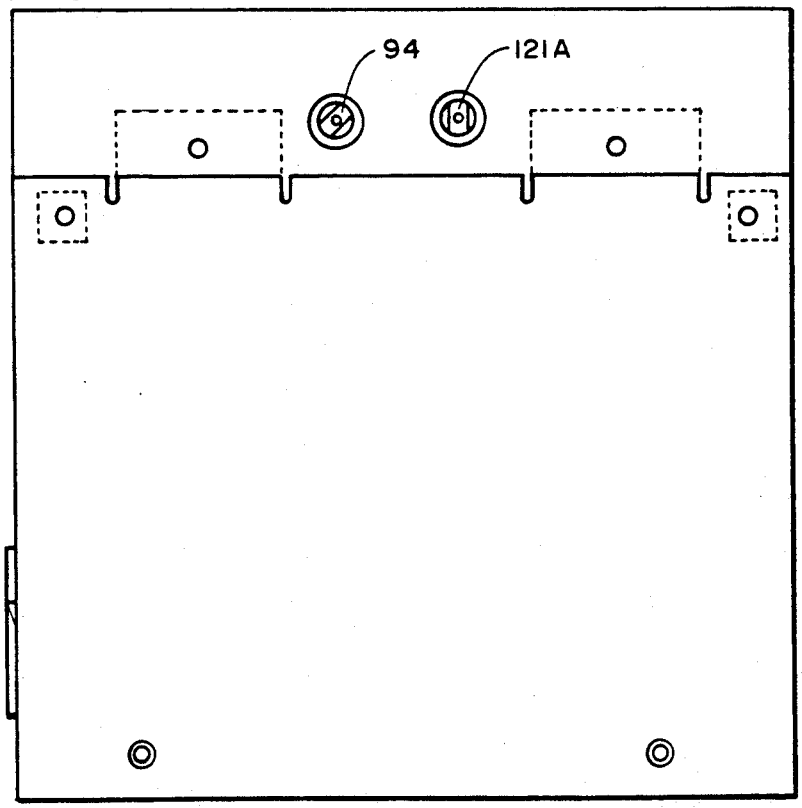
FIG. 13 is a right side elevational view of the embodiment of FIG. 10.

As best shown by FIG. 4, the pressure vessel 24 and breech plug 32 are thermally isolated from the cabinet top 296 by plastic grommet 340 and air gap 342. Insulation 344 thermally isolates heater block 22, pressure vessel 24, all of the valves, connecting tube 68 and sample outlet fitting 94 from the cabinet top 296. The sample outlet fitting 94 is additionally isolated from cabinet top 296 by the radial gap between the fitting 94 and the clearance hole for it 348 within the cabinet top 296 (FIG. 13). Insulation 350 insulates all valves, heater block, pressure vessel 24, the tubes 60, 62, 66 and 68 from the lower outside environment so that they are kept hot by heat originating in the heater block 22.

FIG. 11 is a top view of the cabinet with the breech plugs 32 and 32' removed and with all the valve knobs removed. Grommeted holes from the two breech plugs are shown as 352 and 352'. Holes 354, 356, 354' and 356' are clearance holes for the operating shafts and other protruding parts of valves 54, 54' 124 and 124' respectively. The clearance holes are large enough so that cabinet top 296 does not touch any parts directly connected to the valves. Valves 54 and 54' are fitted with control shaft extension members 294 and 294' because of the additional space required by the gears 84 and 82 (and 84' and 82').

Thermocouple temperature controller 360 (FIGS. 10–13) provides time-proportioned power to heating elements 272 and 272' (FIGS. 5–9). The low energy time-proportioned output of thermocouple temperature controller 360 is used to control a conventional semiconductor switch or relay within the controller which in turn switches the power to the heating elements, which in the preferred embodiment is a total of 800 watts. The sensing thermocouple for providing temperature feedback information to thermocouple temperature controller 360 has an iron-constantan thermocouple junction located within bore 364 (FIGS. 5–9) of the heating block 22. Manual power switch 298 turns the heating circuit on and off. The thermocouple temperature controller, manual power switch and semiconductor switch or relay are located within the case bottom 362. Preferably, a small colling fan located in the case bottom draws outside air through the case bottom.

Figure 14:
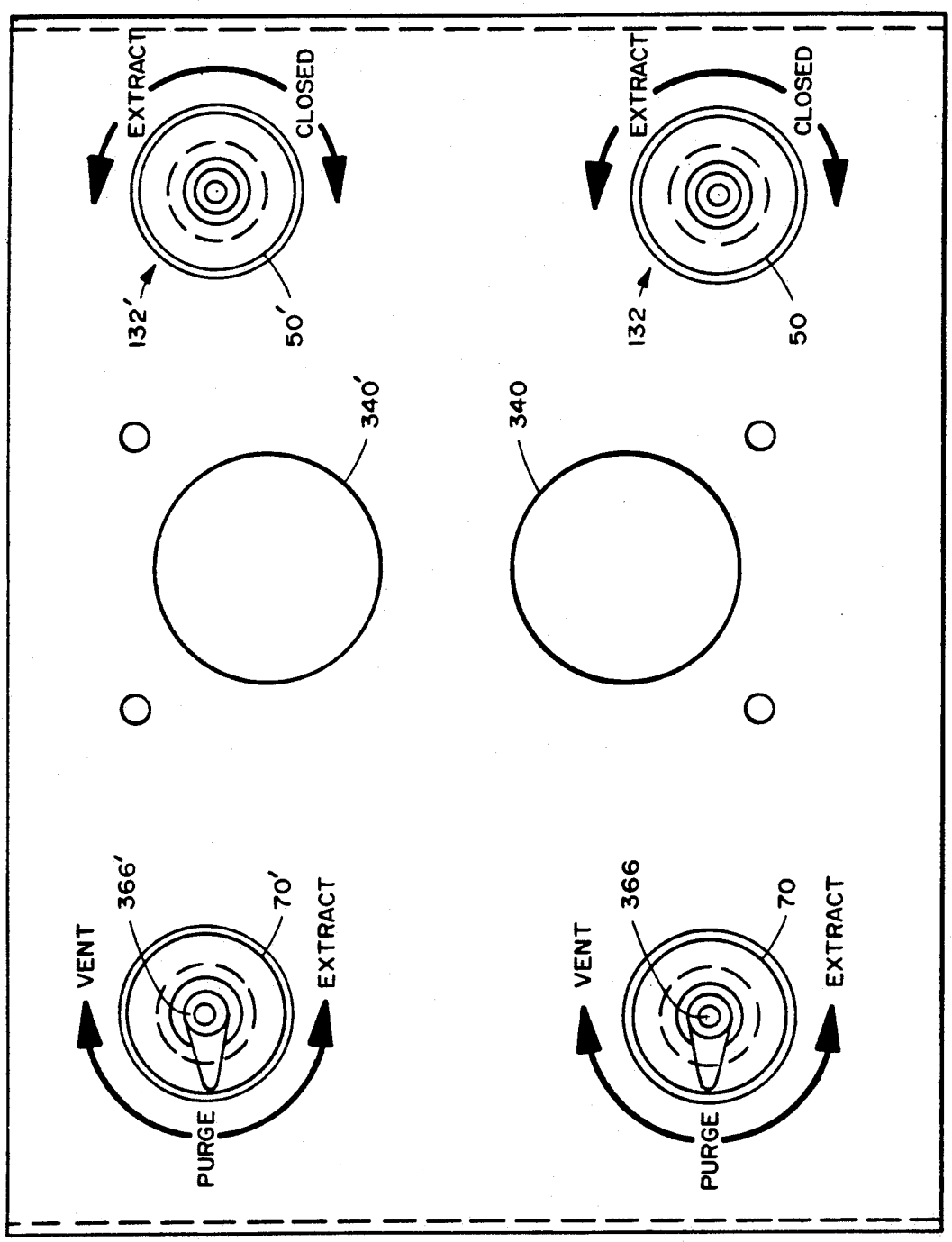
FIG. 14 is a plan view of the cabinet for the embodiment of FIGS. 1-13 illustrating the labeling of the control valves on top of the supercritical fluid extractor.
Figure 12:
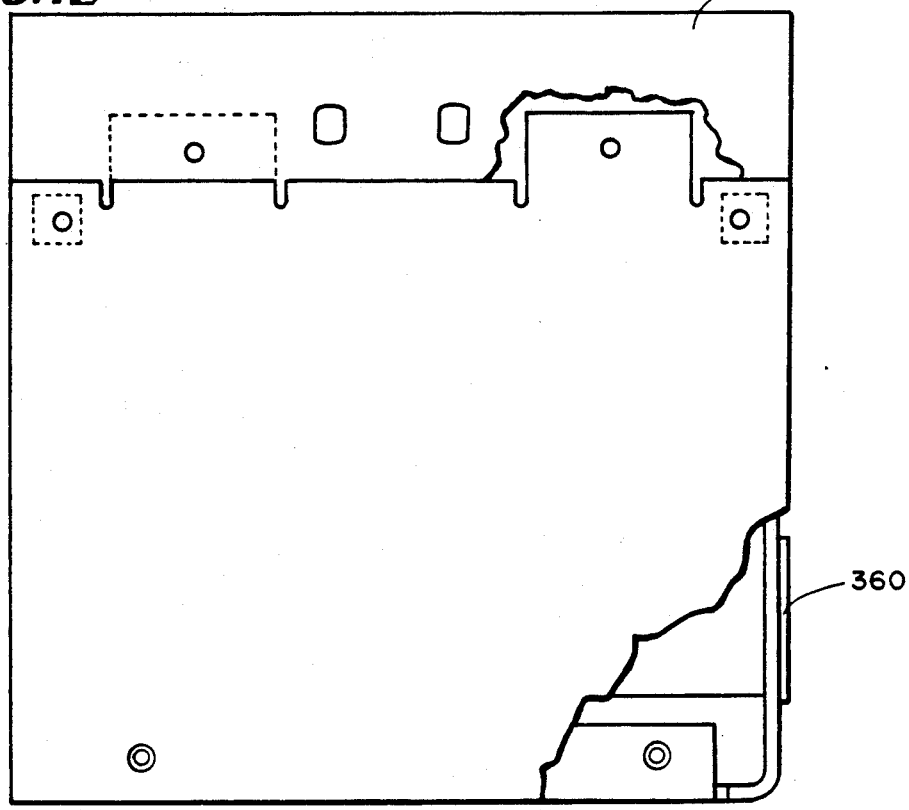
FIG. 12 is an elevational left side view partly broken away of the embodiment of FIG. 10.

FIG. 14 is a top view of the cabinet showing the labeling of the control knobs for the valves. The geared dual valve 54 and 52 (and also 54' and 52' for the second extraction station) has knob 70 with indicating pointer 366. In the "PURGE" (middle) position shown, both valves 54 and 52 are open. In the fully clockwise position with the pointer indicating "VENT", valve 54 is closed and valve 52 is open. In the fully counterclockwise position with the pointer indicating "EXTRACT", valve 54 is open and valve 52 is closed. In regard to control knob 132 connected to valve 124 (and control knob 132' connected to 124'), clockwise rotation of the knob closes the valve and counterclockwise rotation (in the "EXTRACT" direction) opens the valve.

Before using the extraction system 10, the pump 12 is set to the desired pressure and the heater block 22 is set to the desired temperature. The bottom cap 144 (FIG. 2) with the frit 160 is screwed onto the bottom of extraction tube 152. The internal cavity 158 is then filled or partly filled with sample to be extracted. The frit 162 and top cap 174 are then screwed on to the top of extraction tube 152 forming the cartridge and plug assembly 26 (FIG. 3).

The cartridge and plug assembly 26 is then clipped into breech plug 32 by shoving the fitting nipple 176 on the extraction cartridge past garter spring 184 located within breech plug 32. Knob 70 and pointer 366 are set to the "VENT" position (FIG. 14) closing valve 54 and opening valve 52 (FIG. 1). Valve 124 is set to the clockwise ("CLOSED") position.

The assembled breech plug and extraction cartridge are inserted into preheated pressure vessel 22 and manually screwed with knob 34 into pressure vessel 24 until annular flange 190 contacts the top of pressure vessel 24 (FIG. 4). The pressure vessel has been preheated under control of thermocouple temperature controller 360 to the desired temperature. The cartridge and plug assembly 26 within pressure vessel 24 rapidly rises to the required temperature.

After insertion of the cartridge and plug assembly 26 into the sample block 24, valve knob 70 is rotated so that its pointer 366 is at the "PURGE" position. In this position, both valves 54 and 52 are open. Since the pump 12 has already been set to the desired fluid pressure, fluid flows through tubes 76, 56, valve 54, tube 58, heat exchanger 40, tube 60, check valves 60A and 60B and inlet fitting 42 into the cavity 180 (FIG. 4). Since valve 124 is closed, supercritical fluid preheated to the correct temperature by heat exchanger 40, flows past hat-shaped washer 216, fitting nipple 176 and around the outside of cartridge and plug assembly 26 (FIG. 3). This supercritical fluid dissolves any contaminants on the outside of extraction cartridge assembly 30 and any contaminants inside pressure vessel 24. The hot supercritical fluid also insures that the extraction cartridge assembly 30 is at the proper operating temperature. The supercritical fluid flushes the contaminants from fitting 44, through tube 62, valve 52, tube 64, the fitting 50 and the capillary tube 110.

After a short purge cycle, control knob 70 is set so that its pointer 366 points to "EXTRACT" (FIG. 14). This sets valves 54 and 52 so that valve 54 is open and valve 52 is closed. Immediately after making this setting, the operator opens valve 124 by rotating knob 132 counterclockwise in the "EXTRACT" direction indicated on FIG. 14. Pressurized fluid flows through valve 54 into heat exchanger 40 so that it is at the desired supercritical temperature, and flows into fitting 42. It then flows into cavity 180 and past the annular space between shoulder screw 218 and the inside diameter of hat-shaped washer 216, after which it passes through the interior of fitting nipple 176, through passageway 250 and into the extraction vessel 26 (FIG. 3). This supercritical fluid flowing through the interior sample cavity 254 (FIG. 2) of the extraction cartridge extracts analyte from the sample 134 contained within the cavity 254.

Supercritical fluid with the analyte in solution passes out through the fitting 46, the tube 66, the valve 124, the tube 68, the coupling 94 and the capillary tube 128 which leads into the collecting solvent 104 within test tube 98. The analyte is dissolved in the solvent 104 for later analysis. When the extraction is complete knob 132 is rotated clockwise in the "CLOSED" direction, closing valve 124. This stops the flow of supercritical fluid into the extraction cartridge 26. Knob 70 is then rotated clockwise so that its pointer 366 is in the "VENT" position. This closes valve 54 and opens valve 52, depressurizing the pressure vessel 24 and cartridge and plug assembly 26 through capillary tube 110. When bubbles stop issuing through the end of capillary tube 110, despressurization is complete. Knob 54 is rotated counterclockwise to unscrew the breech plug 32 and the attached cartridge and plug assembly 26 from pressure vessel 24. Extraction cartridge assembly 30 may now be open to empty spent sample.

As can be understood from the above description, the supercritical extraction technique has several advantages: (1) it is more convenient than prior art extractors; (2) it includes a self-cleaning feature; and (3) it has, as one component, a disposable inexpensive cartridge.

One reason it is convenient to use is because the cartridge containing the spent sample can be removed while the cartridge is hot because there is a handle that resists being heated and extends outside of the pressure vessel for removal of the cartridge. Another reason it is convenient to use is that it is easier to open the cartridge and pressure vessel since there are no bolts or the like, and in some embodiments, the cartridge is disposable. This convenience is significant because it reduces the time of extraction materially.

It is less expensive because there is pressure equalization within the extractor and the pressure vessel even though it permits purging of the pressure vessel and extraction through separate outlets. A reduction in cost is obtained because plastic cartridges or weaker metal cartridges may be used since the cartridge does not have to withstand a high pressure difference.

Although a preferred embodiment of the invention has been described in some detail, many modifications and variations of the preferred embodiment can be made without deviating from the invention. Therefore, it is to be understood that within the scope of the appended claims the invention may be practiced other than as specifically described.

What is claimed is:

1. Apparatus comprising: Means for enabling supercritical fluid extraction of a sample, said means including:
   pressure vessel means having an interior, an exterior, a first port for fluid entrance and at least a second port for fluid outlet;
   a removable sample holding extraction cartridge which sealedly installs within said pressure vessel means;
   said cartridge having an interior and an exterior;
   said cartridge interior being adapted to hold sample;
   means for distributing said fluid to both the interior and exterior of said cartridge;
   said cartridge having a fluid inlet and a fluid outlet; and
   means for preventing contamination upon the said exterior of the extraction cartridge or the said interior of the pressure vessel from passing through the outlet of the said cartridge.

2. Apparatus for supercritical fluid extraction in accordance with claim 1 in which:
   said pressure vessel first port is coupled by first coupling means to the fluid inlet of the cartridge; and
   said extraction cartridge outlet coupled by second coupling means to the fluid outlet of the pressure vessel.

3. Apparatus according to claim 1 in which said means for preventing contamination from reaching the outlet fitting incorporates means for flushing fluid originating from said inlet across the outside of said extraction cartridge.

4. Apparatus according to claim 3 in which the means for flushing includes means for flushing through a third port serving as a second outlet in the pressure vessel.

5. A method comprising: Enabling supercritical fluid extraction of a sample by the steps of
   placing a sample into the interior of a removable sample holding extraction cartridge;
   sealingly installing said cartridge within a pressure vessel means having an interior, an exterior, a first port for fluid entrance and a second port for fluid outlet wherein said cartridge has an interior and an exterior;
   distributing said fluid to both the interior and exterior of said cartridge wherein said cartridge has a fluid inlet and a fluid outlet; and
   preventing contamination upon said exterior of the extraction cartridge or said interior of the pressure vessel from passing through said outlet of said cartridge.

6. A method for supercritical fluid extraction in accordance with claim 5 further including the steps of:
   coupling said pressure vessel first port by first coupling means to said fluid inlet of said cartridge; and
   coupling said extraction cartridge outlet by second coupling means to said fluid outlet of said pressure vessel.

7. A method according to claim 5 in which the step of preventing contamination from reaching said outlet fitting includes the step of flushing fluid originating from said inlet across the outside of said extraction cartridge.

8. A method according to claim 7 in which the step of flushing includes the step of flushing said fluid through a third port serving as an outlet in said pressure vessel.

* * * * *